United States Patent
McLuckie et al.

(10) Patent No.: US 12,089,515 B2
(45) Date of Patent: Sep. 17, 2024

(54) MONITORING SYSTEM FOR AN AGRICULTURAL IMPLEMENT

(71) Applicant: CNH Industrial America LLC, New Holland, PA (US)

(72) Inventors: Austin Joseph McLuckie, Morris, IL (US); Grant Thomas Macdonald, Hampshire, IL (US); Johnathon Raymond Dienst, Maple Park, IL (US); Brian John Anderson, Yorkville, IL (US)

(73) Assignee: CNH Industrial America LLC, New Holland, PA (US)

( * ) Notice: Subject to any disclaimer, the term of this patent is extended or adjusted under 35 U.S.C. 154(b) by 633 days.

(21) Appl. No.: 17/110,883

(22) Filed: Dec. 3, 2020

(65) Prior Publication Data

US 2022/0174856 A1    Jun. 9, 2022

(51) Int. Cl.
*A01B 63/14* (2006.01)
*A01B 5/06* (2006.01)
(Continued)

(52) U.S. Cl.
CPC ............... *A01B 63/14* (2013.01); *A01B 5/06* (2013.01); *A01B 15/16* (2013.01); *A01C 5/064* (2013.01);
(Continued)

(58) Field of Classification Search
CPC .......... A01B 63/14; A01B 5/06; A01B 15/16; A01C 5/064; G01B 7/14; G01D 5/2291;
(Continued)

(56) References Cited

U.S. PATENT DOCUMENTS

| | | |
|---|---|---|
| 733,593 A | 7/1903 | Poirier |
| 734,017 A | 7/1903 | Brunt |

(Continued)

FOREIGN PATENT DOCUMENTS

| | | |
|---|---|---|
| CN | 201938044 | 8/2011 |
| CN | 204031764 | 12/2014 |

(Continued)

OTHER PUBLICATIONS

S.I. Distributing, Scraper Kit, JD 7200, 1700 W/O Cast Shank, Inside; https://sidist.com/index.cfm?fuseaction=product.display&product_ID=1198; 1 pg; retrieved Mar. 11, 2020.

(Continued)

*Primary Examiner* — Jamie L McGowan
*Assistant Examiner* — Audrey L Lusk
(74) *Attorney, Agent, or Firm* — Rebecca Henkel; Peter K. Zacharias; Rickard K. DeMille (57) ABSTRACT

A monitoring system for an agricultural implement includes a sensor configured to output a sensor signal indicative of a position of at least one scraper of the agricultural implement relative to a surface of at least one respective disc. The at least one scraper is configured to engage the surface of the at least one respective disc to remove accumulated soil from the surface of the at least one respective disc. The monitoring system also includes a controller communicatively coupled to the sensor. The controller is configured to determine an amount of wear on the at least one scraper based on the position of the at least one scraper relative to the surface of the at least one respective disc, and the controller is configured to output a wear signal indicative of the amount of wear on the at least one scraper.

12 Claims, 4 Drawing Sheets

(51) Int. Cl.
*A01B 15/16* (2006.01)
*A01C 5/06* (2006.01)
*G01B 7/14* (2006.01)
*G01D 5/22* (2006.01)
*G01N 27/04* (2006.01)
*G01N 33/24* (2006.01)
*G01P 3/00* (2006.01)

(52) U.S. Cl.
CPC ............. *G01B 7/14* (2013.01); *G01D 5/2291* (2013.01); *G01N 27/04* (2013.01); *G01N 33/24* (2013.01); *G01P 3/00* (2013.01); *G01N 33/245* (2024.05)

(58) Field of Classification Search
CPC .. G01N 27/04; G01N 33/24; G01N 2033/245; G01P 3/00
See application file for complete search history.

(56) References Cited

U.S. PATENT DOCUMENTS

| | | | |
|---|---|---|---|
| 845,425 | A | 2/1907 | Livesay |
| 866,622 | A | 9/1907 | Christman et al. |
| 882,056 | A | 3/1908 | Folkerts |
| 1,113,776 | A | 10/1914 | Goetz |
| 1,129,848 | A | 3/1915 | Cast |
| 1,204,306 | A | 11/1916 | Offerman |
| 1,264,970 | A | 5/1918 | Pfeifer |
| 1,545,895 | A | 7/1925 | Hamilton |
| 2,242,608 | A | 8/1938 | Graves |
| 3,833,067 | A | 9/1974 | Peterson, Jr. et al. |
| 4,034,688 | A | 7/1977 | Ernst |
| 4,113,030 | A | 9/1978 | Walker |
| 4,206,817 | A | 6/1980 | Bowerman |
| 4,337,835 | A | 7/1982 | Steilen |
| 4,603,746 | A | 8/1986 | Swales |
| 4,736,803 | A | 4/1988 | Roush |
| 5,060,586 | A | 10/1991 | Hoyt |
| 6,223,832 | B1 * | 5/2001 | Hook ................. A01B 15/16 172/566 |
| 6,260,632 | B1 | 7/2001 | Bourgault et al. |
| 6,386,127 | B1 | 5/2002 | Prairie et al. |
| 7,290,620 | B2 | 11/2007 | Cooper et al. |
| 7,984,768 | B2 | 7/2011 | Schilling |
| 9,485,900 | B2 | 11/2016 | Connell et al. |
| 9,769,971 | B2 | 9/2017 | Hesla |
| 9,891,155 | B2 | 2/2018 | Eising |
| 10,375,879 | B2 | 8/2019 | Garner et al. |
| 10,481,142 | B2 | 11/2019 | Rhodes et al. |
| 2011/0108296 | A1 * | 5/2011 | Schilling ................ A01B 23/06 111/163 |
| 2014/0216312 | A1 * | 8/2014 | Bassett .................. A01B 15/18 111/121 |
| 2016/0198619 | A1 | 7/2016 | Scolari et al. |
| 2017/0153126 | A1 * | 6/2017 | Wu ........................ F01D 17/145 |
| 2018/0368306 | A1 * | 12/2018 | Hesla ..................... A01B 15/16 |
| 2019/0112924 | A1 * | 4/2019 | Kawai ..................... E21D 9/003 |
| 2019/0124824 | A1 * | 5/2019 | Hubner ................. A01C 5/064 |
| 2019/0230848 | A1 | 8/2019 | Forrest et al. |
| 2020/0267882 | A1 | 8/2020 | McLuckie et al. |
| 2020/0315080 | A1 | 10/2020 | McLuckie et al. |
| 2020/0390024 | A1 * | 12/2020 | Naylor ................. G01N 33/246 |
| 2021/0112699 | A1 * | 4/2021 | Stanhope ............... A01C 5/064 |
| 2022/0117147 | A1 * | 4/2022 | Collin ...................... A01C 7/08 |

FOREIGN PATENT DOCUMENTS

| | | | |
|---|---|---|---|
| CZ | 293891 | | 8/2004 |
| DE | 202007015632 | | 3/2009 |

OTHER PUBLICATIONS

S.I. Distributing, Scraper Kit, CIH 800, 900 Series, Inside, Right, https://sidist.com/index.cfm?fuseaction=product.display&product_ID=1201; 1 pg; retrieved Mar. 11, 2020.

Part #TS455, Tungsten Scraper Kit, Shoup Parts, https://www.shoupparts.com/TS455-Tungsten-Scraper-Kit-For-John-Deere-Grain-Drills, viewed Feb. 5, 2019, 2 pgs.

Part #RDS201, Rotating Disc Scraper, Shoup Parts, https://www.shoupparts.com/RDS201-Rotating-Disc-Scraper, viewed Feb. 5, 2019, 2 pgs.

Air Design, AD21070 John Deere Pro Inside Planter Scrapers, https://www.airdesignscrapers.com/store/index.php?I=product_detail&p=17, viewed Feb. 5, 2019, 1 pg.

Air Design, AD21092 Salford 500 Series Precision Disc Drill Scraper, https://www.airdesignscrapers.com/store/index.php?I=product_detail&p=45, viewed Feb. 5, 2019, 1 pg.

TD16B Tyne Disc Opener Assembly 50x16; http://www.bossagparts.com.au/TD16-Tyne-DIsc-Opener-50-X-16-Assembly; 2 pgs; accessed Jan. 21, 2019.

* cited by examiner

MONITORING SYSTEM FOR AN AGRICULTURAL IMPLEMENT

BACKGROUND

The present disclosure relates generally to a monitoring system for an agricultural implement.

Generally, planting implements (e.g., planters) are towed behind a tractor or other work vehicle via a mounting bracket secured to a rigid frame of the implement. Planting implements typically include multiple row units distributed across a width of the implement. Each row unit is configured to deposit seeds at a desired depth beneath the soil surface of a field, thereby establishing rows of planted seeds. For example, each row unit typically includes a ground engaging tool or opener that forms a seeding path (e.g., trench) for seed deposition into the soil. An agricultural product conveying system (e.g., seed tube or powered agricultural product conveyor) is configured to deposit seeds and/or other agricultural products (e.g., fertilizer) into the trench. The opener/agricultural product conveying system is followed by closing discs that move displaced soil back into the trench and/or a packer wheel that packs the soil on top of the deposited seeds/other agricultural products.

Certain row units include a scraper assembly having an inner scraper configured to remove accumulated soil from an inner surface of the ground engaging tool/opener and/or an outer scraper configured to remove accumulated soil from an outer surface of the ground engaging tool/opener. For example, the ground engaging tool/opener may include an opener disc, and soil may accumulate on the inner surface and/or the outer surface of the opener disc during formation of the seeding path/trench. Accordingly, an inner scraper of the scraper assembly may contact the inner surface of the opener disc, and/or an outer scraper of the scraper assembly may contact the outer surface of the opener disc, thereby removing accumulated soil from the respective surface(s) of the opener disc during formation of the seeding path/trench. Unfortunately, in certain soil conditions, the inner/outer scraper may not effectively remove all of the accumulated soil from the respective surface of the opener disc. As a result, the accumulated soil may interfere with rotation of the opener disc, thereby reducing the effectiveness of the planting process. In addition, each scraper may wear over time, thereby reducing the effectiveness of the scraper.

BRIEF DESCRIPTION

In certain embodiments, a monitoring system for an agricultural implement includes a sensor configured to output a sensor signal indicative of a position of at least one scraper of the agricultural implement relative to a surface of at least one respective disc. The at least one scraper is configured to engage the surface of the at least one respective disc to remove accumulated soil from the surface of the at least one respective disc. The monitoring system also includes a controller having a memory and a processor. The controller is communicatively coupled to the sensor, the controller is configured to determine an amount of wear on the at least one scraper based on the position of the at least one scraper relative to the surface of the at least one respective disc, and the controller is configured to output a wear signal indicative of the amount of wear on the at least one scraper.

DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

One or more specific embodiments of the present disclosure will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements. Any examples of operating parameters and/or environmental conditions are not exclusive of other parameters/conditions of the disclosed embodiments.

Figure 1:
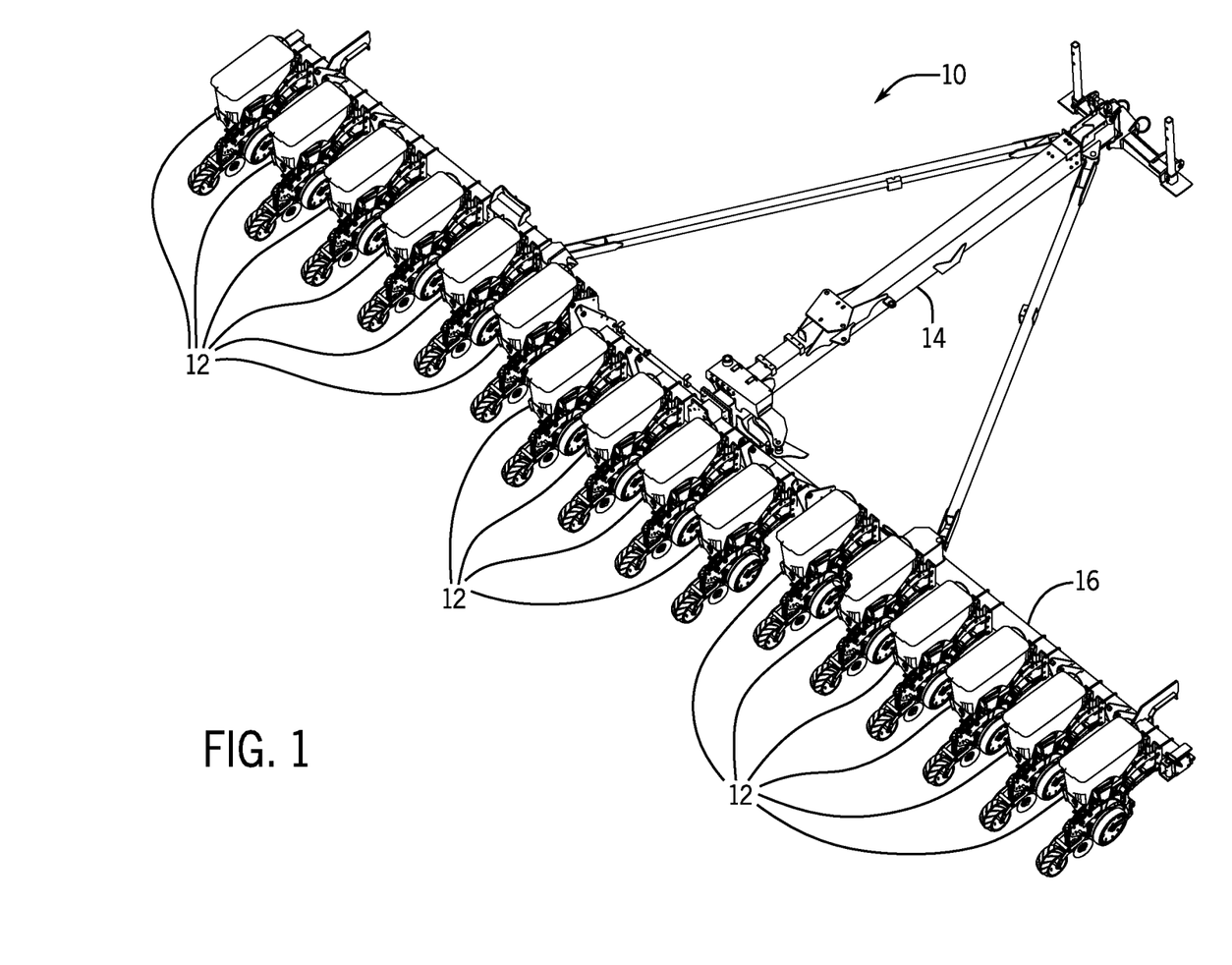
FIG. 1 is a perspective view of an embodiment of an agricultural implement having multiple row units distributed across a width of the agricultural implement.

FIG. 1 is a perspective view of an embodiment of an agricultural implement 10 (e.g., planting implement) having multiple row units 12 distributed across a width of the agricultural implement 10. The agricultural implement 10 is configured to be towed through a field behind a work vehicle, such as a tractor. As illustrated, the agricultural implement 10 includes a tongue assembly 14, which includes a hitch configured to couple the agricultural implement 10 to an appropriate tractor hitch (e.g., via a ball, clevis, or other coupling). The tongue assembly 14 is coupled to a tool bar 16 which supports multiple row units 12. Each row unit 12 may include one or more opener discs configured to form a seed path (e.g., trench) within soil of a field. The row unit 12 may also include an agricultural product conveying system (e.g., seed tube or powered agricultural product conveyer) configured to deposit seeds and/or other agricultural product(s) (e.g., fertilizer) into the seed path/trench. In addition, the row unit 12 may include closing disc(s) and/or a packer wheel positioned behind the agricultural product conveying system. The closing disc(s) are configured to move displaced soil back into the seed path/trench, and the packer wheel is configured to pack soil on top of the deposited seeds/other agricultural product(s).

During operation of the row units 12, clumps of soil may accumulate on the opener disc(s) (e.g., due to moist soil conditions, etc.). Accordingly, in certain embodiments, at least one row unit 12 may include a scraper assembly configured to remove accumulated soil from the opener disc(s) as the opener disc(s) form the seed path/trench. As discussed in detail below, the scraper assembly may include an inner scraper engaged with an inner surface of a respective opener disc and configured to remove accumulated soil from the inner surface of the respective opener disc, and the scraper assembly may include an outer scraper engaged with an outer surface of the respective opener disc and configured to remove accumulated soil from the outer surface of the respective opener disc.

In certain embodiments, the implement includes a monitoring system configured to determine an amount of wear on one or more scrapers, to identify an operational inefficiency of at least one row unit, to determine one or more soil properties of the soil, or a combination thereof. For example, in certain embodiments, a monitoring system includes a sensor configured to output a sensor signal indicative of a position of at least one scraper relative to a surface of at least one respective disc (e.g., opener disc). As discussed above, the at least one scraper is configured to engage the surface of the at least one respective disc to remove accumulated soil from the surface of the at least one respective disc. In addition, the monitoring system includes a controller having a memory and a processor, in which the controller is communicatively coupled to the sensor. The controller is configured to determine an amount of wear on the at least one scraper based on the position of the at least one scraper relative to the surface of the at least one respective disc. The controller is also configured to output a wear signal indicative of the amount of wear on the at least one scraper. In certain embodiments, the wear signal may be output to a user interface, and the user interface may inform an operator of the implement of the amount of wear on the at least one scraper, thereby enabling the operator to perform maintenance operations (e.g., replacing the at least one scraper, adjusting the force applied by a biasing member to the at least one scraper, etc.).

Furthermore, in certain embodiments, a monitoring system includes a first sensor configured to output a first sensor signal indicative of a first rotational speed of a first disc (e.g., first opener disc) of a row unit. The monitoring system also includes a second sensor configured to output a second sensor signal indicative of a second rotational speed of a second disc (e.g., second opener disc) of the row unit, in which the first and second discs are positioned adjacent to one another and configured to cooperatively excavate a trench within the soil. In addition, the monitoring system includes a controller having a memory and a processor, in which the controller is communicatively coupled to the first sensor and to the second sensor. The controller is configured to determine a rotational speed difference between the first rotational speed of the first disc and the second rotational speed of the second disc. In addition, the controller is configured to detect an operational inefficiency (e.g., soil accumulation on one of the discs, an undesirably large force applied by a scraper to one of the discs, etc.) in response to determining that the rotational speed difference is greater than a rotational speed difference threshold value. The controller is also configured to output an operational inefficiency signal in response to detecting the operational inefficiency. In certain embodiments, the operational inefficiency signal may be output to a user interface, and the user interface may inform the operator of the implement of the detected operational inefficiency, thereby enabling the operator to perform maintenance operations (e.g., adjusting the force applied by a biasing member to a scraper engaged with one of the discs, manually removing accumulated soil from one or the discs, etc.).

In addition, in certain embodiments, a monitoring system includes a sensor configured to be positioned proximate to a disc (e.g., opener disc) and remote from the soil. The disc is configured to excavate a trench within the soil as the disc rotates relative to the sensor, the sensor is configured to receive soil from a surface of the disc as the disc rotates, and the sensor is configured to output a sensor signal indicative of at least one property of the soil. In addition, the monitoring system includes a controller having a memory and a processor, in which the controller is communicatively coupled to the sensor. The controller is configured to receive the sensor signal and to determine the at least one property of the soil. The controller is also configured to output a soil property signal indicative of the at least one soil property. In certain embodiments, the soil property signal may be output to a user interface, and the user interface may inform the operator of the at least one soil property, thereby enabling the operator to manually adjust operation of the implement based on the at least one soil property. Furthermore, in certain embodiments, the soil property signal may be output to one or more actuators, and the soil property signal may be indicative of instructions to control the one or more actuators to adjust operation of the implement.

Figure 2:
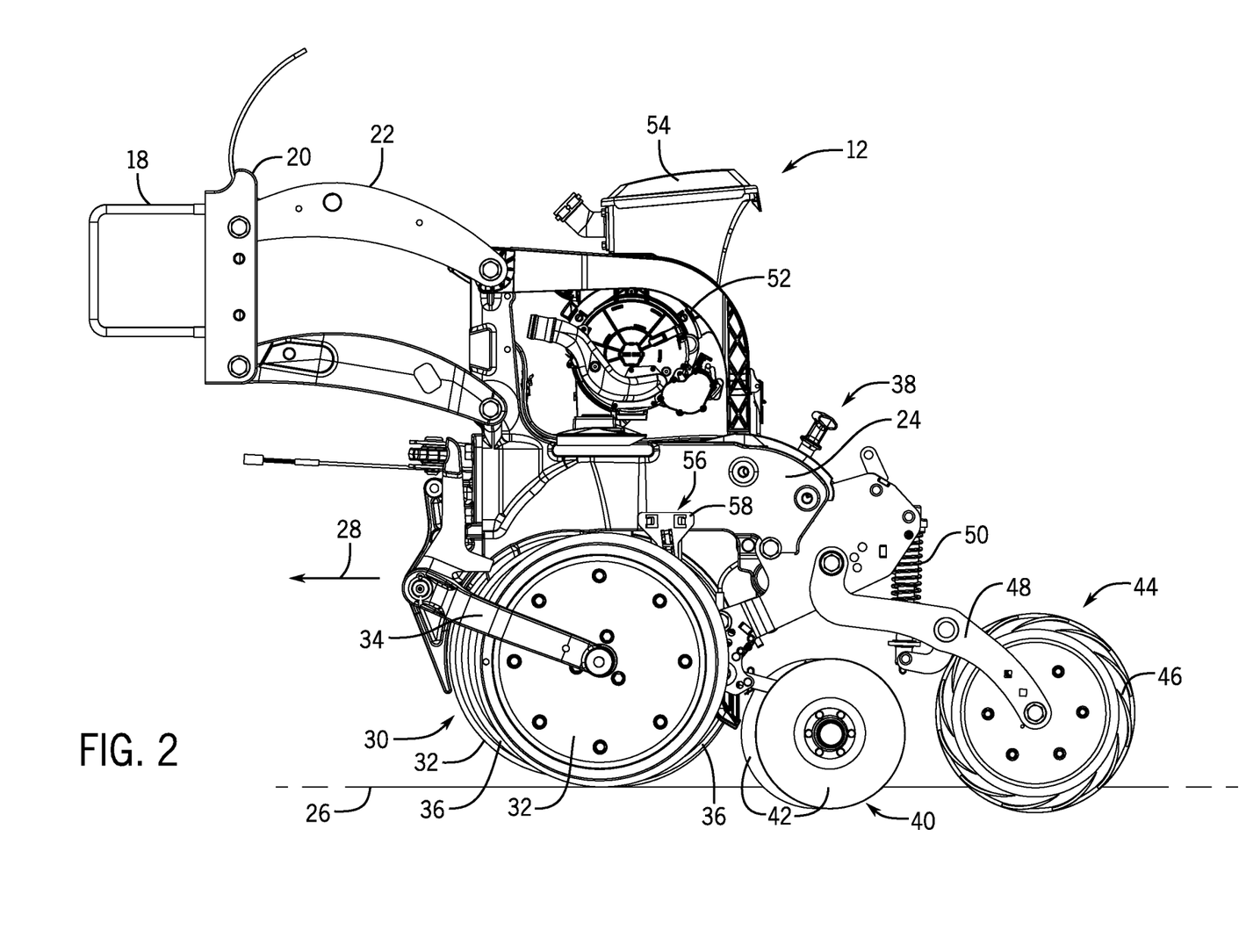
FIG. 2 is a side view of an embodiment of a row unit that may be employed on the agricultural implement of FIG. 1.

FIG. 2 is a side view of an embodiment of a row unit 12 (e.g., agricultural row unit) that may be employed on the agricultural implement of FIG. 1. The row unit 12 includes a mount 18 configured to secure the row unit 12 to the tool bar of the agricultural implement. In the illustrated embodiment, the mount 18 includes a u-bolt that secures a bracket 20 of the row unit 12 to the tool bar. However, in alternative embodiments, the mount may include another suitable device that couples the row unit to the tool bar. A linkage assembly 22 extends from the bracket 20 to a frame 24 of the row unit 12. The linkage assembly 22 is configured to enable vertical movement of the frame 24 relative to the tool bar in response to variations in a soil surface 26. In certain embodiments, a down pressure system (e.g., including a hydraulic actuator, a pneumatic actuator, etc.) may be coupled to the linkage assembly 22 and configured to urge the frame 24 toward the soil surface 26. While the illustrated linkage assembly 22 is a parallel linkage assembly (e.g., a four-bar linkage assembly), in other embodiments, another suitable linkage assembly may extend between the bracket and the frame.

The row unit 12 is configured to deposit seeds and/or other agricultural product(s) at a desired depth beneath the soil surface 26 as the row unit 12 traverses a field along a direction of travel 28. The row unit 12 includes an opener assembly 30 that forms a trench in the soil for seed/other agricultural product deposition into the soil. In the illustrated embodiment, the opener assembly 30 includes gauge wheels 32, arms 34 that pivotally couple the gauge wheels 32 to the frame 24, and opener discs 36. The opener discs 36 are configured to excavate a trench into the soil, and the gauge wheels 32 are configured to control a penetration depth of the opener discs 36 into the soil. In the illustrated embodiment, the row unit 12 includes a depth control system 38 configured to control the vertical position of the gauge wheels 32 (e.g., by blocking rotation of the arms in the upward direction beyond a selected orientation), thereby controlling the penetration depth of the opener discs 36 into the soil.

The row unit 12 also includes an agricultural product conveying system (e.g., seed tube or powered agricultural product conveyor) configured to deposit seeds and/or other agricultural product(s) (e.g., fertilizer) into the trench. The opener assembly 30 and the agricultural product conveying system are followed by a closing assembly 40 that moves displaced soil back into the trench. In the illustrated embodiment, the closing assembly 40 includes two closing discs 42. However, in other embodiments, the closing assembly may include other suitable closing device(s) (e.g., a single closing disc, etc.). In addition, in certain embodiments, the closing assembly may be omitted. In the illustrated embodiment, the closing assembly 40 is followed by a packing assembly 44 configured to pack soil on top of the deposited seeds and/or other agricultural product(s). The packing assembly 44 includes a packer wheel 46, an arm 48 that pivotally couples the packer wheel 46 to the frame 24, and a biasing member 50 configured to urge the packer wheel 46 toward the soil surface 26, thereby enabling the packer wheel to pack soil on top of the deposited seeds and/or other agricultural product(s). While the illustrated biasing member 50 includes a spring, in other embodiments, the biasing member may include another suitable biasing device, such as a hydraulic cylinder or a pneumatic cylinder, among others. Furthermore, in certain embodiments, the packing assembly may be omitted.

The row unit 12 includes a vacuum seed meter 52 configured to receive agricultural product (e.g., seeds) from a hopper 54. In certain embodiments, the vacuum seed meter 52 includes a disc having multiple openings. An air pressure differential between opposite sides of the disc induces the agricultural product (e.g., seeds) to be captured within the openings. As the disc rotates, the agricultural product is conveyed toward the agricultural product conveying system. When the agricultural product (e.g., seed) is aligned with an inlet to the agricultural product conveying system, the air pressure on each side of the disc is substantially equalized (e.g., at the end of a vacuum passage), thereby enabling the agricultural product (e.g., seed) to enter the agricultural product conveying system (e.g., seed tube or powered agricultural product conveyor). The agricultural product conveying system then directs the agricultural product to the trench. While the illustrated embodiment includes a vacuum seed meter, in other embodiments, other suitable seed/agricultural product meters may be utilized. As used herein, "vacuum" refers to an air pressure that is less than the ambient atmospheric air pressure, and not necessarily 0 pa.

In the illustrated embodiment, the row unit 12 includes a scraper assembly 56 having an outer scraper 58 (e.g., first outer scraper) coupled to the frame 24 and configured to engage an outer surface of an opener disc 36 (e.g., first disc). Furthermore, as discussed in detail below, the scraper assembly 56 includes an inner scraper (e.g., first inner scraper) configured to engage an inner surface of the opener disc 36. Because the scraper assembly 56 includes an inner scraper and an outer scraper 58, accumulated soil may be removed from both sides of the opener disc 36, thereby enhancing the accuracy and efficiency of the seed path/trench forming process. Furthermore, in certain embodiments, the scraper assembly may include a second inner scraper and a second outer scraper configured to remove accumulated soil from a second opener disc of the row unit.

In certain embodiments, a monitoring system may be used to determine an amount of wear on one or more of the scrapers. For example, the monitoring system may include a sensor configured to output a sensor signal indicative of a position of a scraper relative to a surface of a respective disc, and a controller may determine an amount of wear on the scraper based on the position. Furthermore, in certain embodiments, the monitoring system may be used to identify an operational inefficiency of the row unit. For example, the monitoring system may include sensors configured to determine rotational speeds of two adjacent discs (e.g., opener discs) of the row unit, and a controller may detect an operational inefficiency based on a rotational speed difference between the two adjacent discs. In addition, in certain embodiments, the monitoring system may be used to determine one or more soil properties of the soil. For example, the monitoring system may include a sensor positioned proximate to a disc and remote from the soil, in which the sensor is configured to output a sensor signal indicative of one or more soil properties. A controller of the monitoring system may receive the sensor signal and determine the one or more soil properties.

Figure 3:
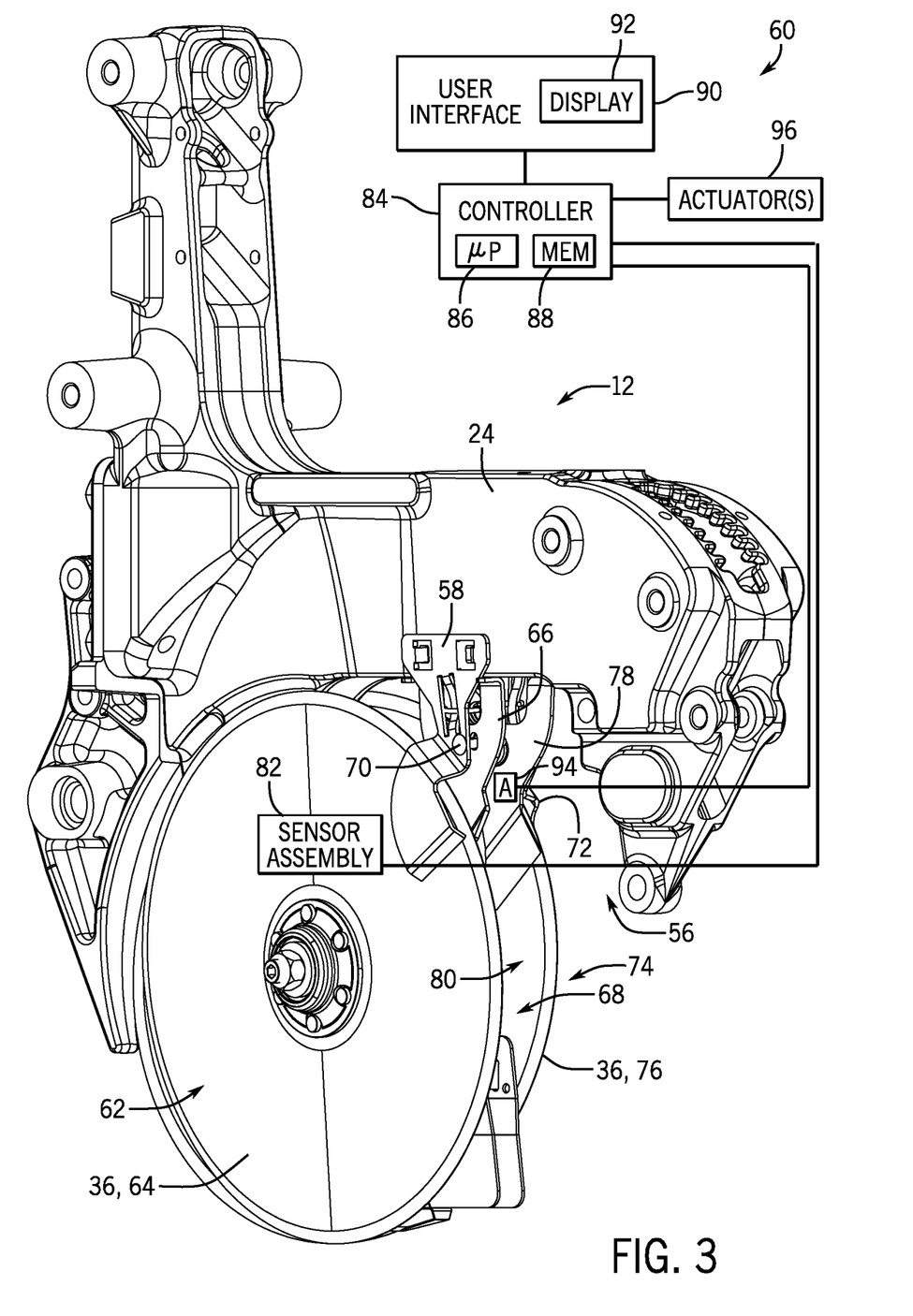
FIG. 3 is a perspective view of a portion of the row unit of FIG. 2, including an embodiment of a monitoring system.

FIG. 3 is a perspective view of a portion of the row unit 12 of FIG. 2, including an embodiment of a monitoring system 60. In the illustrated embodiment, the scraper assembly 56 includes a first outer scraper 58 configured to engage an outer surface 62 of a first opener disc 64, and the scraper assembly 56 includes a first inner scraper 66 configured to engage an inner surface 68 of the first opener disc 64. Furthermore, the first outer scraper 58 is coupled to the frame 24 of the row unit 12. The scraper assembly 56 also includes a fastener 70 that couples the first inner scraper 66 to the first outer scraper 58. In addition, the first inner scraper 66 has an engagement feature (e.g., at least one arm) in contact with the first outer scraper 58 and/or the frame 24 to block rotation of the first inner scraper 66 about the first fastener 70 relative to the first outer scraper 58.

In the illustrated embodiment, the scraper assembly 56 also includes a second outer scraper 72 coupled to the frame 24 of the row unit 12 and configured to engage an outer surface 74 of a second opener disc 76. In addition, the scraper assembly 56 includes a second inner scraper 78 configured to engage an inner surface 80 of the second opener disc 76. Furthermore, the scraper assembly 56 includes a second fastener that couples the second inner scraper 78 to the second outer scraper 72. Similar to the first inner scraper 66, the second inner scraper 78 has an engagement feature (e.g., at least one arm) in contact with the second outer scraper 72 and/or the frame 24 of the row unit 12 to block rotation of the second inner scraper 78 about the second fastener relative to the second outer scraper 72. While the scraper assembly 56 includes two pairs of inner/outer scrapers in the illustrated embodiment, in other embodiments, the scraper assembly may include more or fewer pairs of inner/outer scrapers (e.g., 1, 2, 3, 4, 5, 6, or more). For example, the scraper assembly may include one pair of inner/outer scrapers for each opener disc of the row unit. Because the scraper assembly 56 includes an inner scraper and an outer scraper for each opener disc 36, accumulated soil may be removed from both the inner surface and the outer surface of each opener disc 36. As a result, the accuracy and efficiency of the seed path/trench forming process may be enhanced (e.g., as compared to a scraper assembly having only inner scraper(s) or only outer scraper(s)).

In the illustrated embodiment, the monitoring system 60 includes a sensor assembly 82 and a controller 84. As discussed in detail below, the sensor assembly 82 may include a scraper position sensor configured to output a sensor signal indicative of a position of at least one scraper relative to a surface of at least one respective disc. In addition, in certain embodiments, the sensor assembly 82 may include disc speed sensors configured to output respective sensor signals indicative of the rotational speeds of the openers discs. Furthermore, in certain embodiments, the sensor assembly 82 may include a soil sensor positioned proximate to a respective opener disc and remote from the soil, in which the soil sensor is configured to output a sensor signal indicative of at least one property of the soil. Each sensor of the sensory assembly 82 is communicatively coupled to the controller 84, as illustrated.

In certain embodiments, the controller 84 is an electronic controller having electrical circuitry configured to receive the sensor signal(s) from sensor(s) of the sensor assembly 82. In the illustrated embodiment, the controller 84 includes a processor, such as the illustrated microprocessor 86, and a memory device 88. The controller 84 may also include one or more storage devices and/or other suitable components. The processor 86 may be used to execute software, such as software for determining an amount of wear on one or more scrapers, identifying an operational inefficiency of the row unit, determining one or more soil properties of the soil, and so forth. Moreover, the processor 86 may include multiple microprocessors, one or more "general-purpose" microprocessors, one or more special-purpose microprocessors, and/or one or more application specific integrated circuits (ASICS), or some combination thereof. For example, the processor 86 may include one or more reduced instruction set (RISC) processors.

The memory device 88 may include a volatile memory, such as random access memory (RAM), and/or a nonvolatile memory, such as read-only memory (ROM). The memory device 88 may store a variety of information and may be used for various purposes. For example, the memory device 88 may store processor-executable instructions (e.g., firmware or software) for the processor 86 to execute, such as instructions for determining an amount of wear on one or more scrapers, identifying an operational inefficiency of the row unit, determining one or more soil properties of the soil, and so forth. The storage device(s) (e.g., nonvolatile storage) may include ROM, flash memory, a hard drive, or any other suitable optical, magnetic, or solid-state storage medium, or a combination thereof. The storage device(s) may store data, instructions (e.g., software or firmware for determining an amount of wear on one or more scrapers, identifying an operational inefficiency of the row unit, determining one or more soil properties of the soil, etc.), and any other suitable data.

In the illustrated embodiment, the monitoring system 60 includes a user interface 90 communicatively coupled to the controller 84. The user interface 90 may include one or more suitable controls configured to receive input from an operator. In addition, the user interface 90 may include one or more suitable interfaces configured to present information to the operator. For example, in the illustrated embodiment, the user interface 90 includes a display 92 configured to present visual information to the operator. In addition, in certain embodiments, the display 92 may include a touch screen interface configured to receive input from the operator.

In certain embodiments, the sensor assembly 82 includes a scraper position sensor configured to output a sensor signal indicative of a position of at least one scraper relative to a surface of at least one respective disc. In such embodiments, the scraper position sensor is communicatively coupled to the controller 84, and the controller is configured to determine an amount of wear on the at least one scraper based on the position of the at least one scraper relative to the surface of the at least one respective disc. For example, as a scraper wears, a respective biasing member may drive the scraper (e.g., a distal end portion of the scraper) toward the surface of the respective disc.

Once the controller 84 determines the amount of wear on the at least one scraper, the controller 84 may output a wear signal indicative of the amount of wear. In certain embodiments, the controller may output the wear signal to the user interface 90, and the user interface 90 (e.g., the display 92 of the user interface 90) may provide an indication to the operator of the amount of wear on the at least one scraper. Accordingly, the operator may determine the amount of wear on one or more scrapers without terminating agricultural operations. Furthermore, in certain embodiments, the monitoring system 60 may include an actuator assembly 94 having one or more scraper actuators configured to control magnitude(s) of force(s) applied by one or more scrapers to the surface(s) of the respective disc(s). In such embodiments, the scraper actuator(s) of the actuator assembly 94 are communicatively coupled to the controller 84, and the controller is configured to control the scraper actuator(s) to control the magnitude(s) of the force(s) applied by the one or more scrapers to the surface(s) of the respective disc(s) based on the amount of wear on the scraper(s) (e.g., the wear signal(s) output by the controller are indicative of instructions to control the magnitude(s) of the force(s)). For example, as a scraper wears, the magnitude of the force applied by the respective biasing member may decrease (e.g., due to elongation of the biasing member). Accordingly, the controller may instruct the respective scraper actuator to compress the biasing member as the scraper wears to substantially maintain the contact force between the scraper and the surface of the respective disc.

In certain embodiments, the sensor assembly 82 includes a first disc speed sensor configured to output a first sensor signal indicative of a first rotational speed of the first opener disc 64 and a second disc speed sensor configured to output a second sensor signal indicative of a second rotational speed of the second opener disc 76. In such embodiments, the first and second disc speed sensors are communicatively coupled to the controller 84, and the controller is configured to determine a rotational speed difference between the first rotational speed and the second rotational speed. In addition, the controller is configured to detect an operational inefficiency in response to determining that the rotational speed difference is greater than a rotational speed difference threshold value. The operational inefficiency may include a scraper applying an undesirably large contact force to the surface of a respective disc, a worn bearing that facilitates rotation of a respective disc, substantial accumulation of soil between a scraper and the surface of a respective disc, one or more other operational inefficiencies that may reduce the rotational speed of a respective disc, or a combination thereof. Once the controller 84 detects the operational inefficiency, the controller 84 may output an operational inefficiency signal. In certain embodiments, the operational inefficiency signal may be output to the user interface 90, and the user interface 90 may inform the operator of the implement of the detected operational inefficiency (e.g., by presenting an indication on the display 92), thereby enabling the operator to perform maintenance operations (e.g., adjusting the force applied by a biasing member to a scraper engaged with a respective disc, manually removing accumulated soil from one of the discs, replacing a worn bearing that facilitates rotation of a respective disc, etc.).

In certain embodiments, the sensor assembly 82 includes a soil sensor positioned proximate to a respective opener disc and remote from the soil, in which the soil sensor is configured to output a sensor signal indicative of at least one property of the soil. In such embodiments, the soil sensor is communicatively coupled to the controller 84, and the controller is configured to determine the at least one property of the soil based on the sensor signal from the soil sensor. The controller is also configured to output a soil property signal indicative of the at least one soil property. In certain embodiments, the soil property signal may be output to the user interface 90, and the user interface 90 may inform the operator of the at least one soil property (e.g., the display 92 of the user interface 90 may present a visual indication of the at least one soil property), thereby enabling the operator to manually adjust operation of the implement based on the at least one soil property. Furthermore, in certain embodiments, the soil property signal may be output to one or more actuators 96, and the soil property signal may be indicative of instructions to control the one or more actuators 96 to adjust operation of the implement. For example, the controller may control one or more downforce actuators based on a detected moisture content of the soil, the controller may control one or more metering actuators to control seed spacing based on a detected nutrient content of the soil, the controller may control one or more penetration depth actuators based on a firmness of the soil, the controller may control other suitable actuator(s) based on certain soil property/properties, or a combination thereof.

Figure 4:
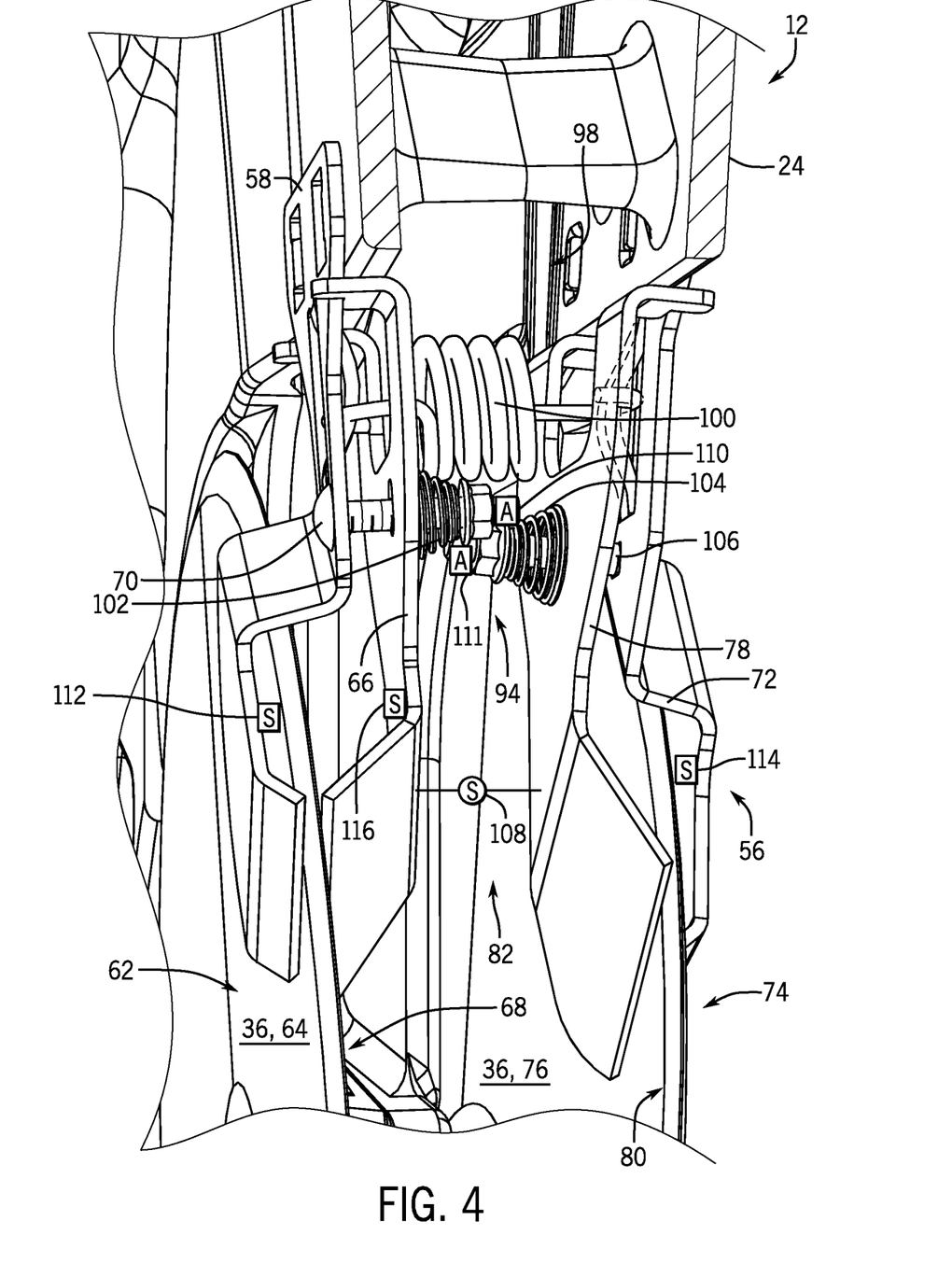
FIG. 4 is a perspective view of a portion of the row unit of FIG. 2, including an embodiment of a sensor assembly and an embodiment of an actuator assembly that may be employed within the monitoring system of FIG. 3.

FIG. 4 is a perspective view of a portion of the row unit 12 of FIG. 2, including an embodiment of a sensor assembly 82 and an embodiment of an actuator assembly 94 that may be employed within the monitoring system of FIG. 3. As illustrated, the first outer scraper 58 is in contact with the outer surface 62 of the first opener disc 64, and the first inner scraper 66 is in contact with the inner surface 68 of the first opener disc 64. Accordingly, the first outer scraper 58 may remove accumulated soil from the outer surface 62 of the first opener disc 64, and the first inner scraper 66 may remove accumulated soil from the inner surface 68 of the first opener disc 64. In addition, the second outer scraper 72 is in contact with the outer surface 74 of the second opener disc 76, and the second inner scraper 78 is in contact with the inner surface 80 of the second opener disc 76. Accordingly, the second outer scraper 72 may remove accumulated soil from the outer surface 74 of the second opener disc 76, and the second inner scraper 78 may remove accumulated soil from the inner surface 80 of the second opener disc 76.

In the illustrated embodiment, the scraper assembly 56 includes a biasing system 98 coupled to the first outer scraper 58 and to the second outer scraper 72. The biasing system 98 is configured to urge the first outer scraper 58 toward the first opener disc 64, and the biasing system 98 is configured to urge the second outer scraper 72 toward the second opener disc 76. Accordingly, the biasing system urges contact between the first outer scraper 58 and the outer surface 62 of the first opener disc 64 and between the second outer scraper 72 and the outer surface 74 of the second opener disc 76. In the illustrated embodiment, the biasing system 98 includes a coil spring 100 having a first end coupled to the first outer scraper 58 and a second end coupled to the second outer scraper 72. However, in other embodiments, the biasing system may include other and/or additional elements configured to urge the outer scrapers toward the respective opener discs. For example, the biasing system may include one or more coil springs, one or more springs of another suitable type (e.g., leaf spring(s), etc.), one or more other suitable biasing elements (e.g., an elastic polymeric element, etc.), or a combination thereof. Furthermore, in certain embodiments, the biasing system may include a first biasing element extending between the frame and the first outer scraper and configured to urge the first outer scraper toward the first opener disc, and the biasing system may include a second biasing element extending between the frame and the second outer scraper and configured to urge the second outer scraper toward the second opener disc.

In the illustrated embodiment, the scraper assembly 56 includes a first biasing member 102 configured to urge the first inner scraper 66 toward the first opener disc 64. In addition, the scraper assembly 56 includes a second biasing member 104 configured to urge the second inner scraper 78 toward the second opener disc 76. In the illustrated embodiment, the first biasing member 102 includes a first coil spring disposed about the first fastener 70, and the second biasing member 104 includes a second coil spring disposed about the second fastener 106. However, in other embodiments, at least one of the biasing members may include another and/or an additional element configured to urge the respective inner scraper toward the respective opener disc. Urging each inner scraper toward the respective opener disc enables the inner scraper to remove accumulated soil from the inner surface of the respective opener disc. In addition, because each inner scraper is urged toward the respective opener disc, contact between the inner scraper and the respective opener disc may be substantially maintained during operation of the row unit (e.g., as compared to an inner scraper that is fixed to the frame and wears over time, thereby establishing a gap between the inner scraper and the respective opener disc).

In the illustrated embodiment, the sensor assembly 82 includes a scraper position sensor 108 (e.g., second sensor, third sensor). The scraper position sensor 108 may be communicatively coupled to the controller, as disclosed above with reference to FIG. 3. In the illustrated embodiment, the scraper position sensor 108 is coupled to the first inner scraper 66 and to the second inner scraper 78. In addition, the scraper position sensor 108 is configured to output a sensor signal (e.g., second sensor signal, third sensor signal) indicative of a distance between the first inner scraper 66 and the second inner scraper 78. The sensor signal indicative of the distance between the first and second inner scrapers is also indicative of the positions of the scrapers relative to the inner surfaces of the respective discs (e.g., because the scrapers move away from one another as the scrapers move toward the inner surfaces of the respective discs). The controller is configured to receive the sensor signal and to determine an amount of wear on the first inner scraper 66 and/or an amount of wear on the second inner scraper 78 based on the distance between the first inner scraper and the second inner scraper. For example, as the first inner scraper 66 wears, the first biasing member 102 drives the first inner scraper 66 (e.g., a distal end portion of the first inner scraper) toward the inner surface 68 of the first opener disc 64. In addition, as the second inner scraper 78 wears, the second biasing member 104 drives the second inner scraper 78 (e.g., a distal end portion of the second inner scraper) toward the inner surface 80 of the second opener disc 76. Accordingly, as the first and/or second inner scraper wears, the distance between the first and second inner scrapers (e.g., the distal end portions of the first and second inner scrapers) increases. As a result, the controller may determine the amount of wear on the first inner scraper and/or the second inner scraper based on the distance between the first and second inner scrapers.

While the scraper position sensor 108 is coupled to the first inner scraper 66 and to the second inner scraper 78 in the illustrated embodiment, in other embodiments, the scraper position sensor may be coupled to another suitable portion of the row unit (e.g., the frame, etc.). For example, in certain embodiments, the scraper position sensor may include a non-contact sensor (e.g., optical sensor, infrared sensor, radio frequency sensor, ultrasonic sensor, etc.) coupled to the frame and configured to output a signal indicative of the distance between the first and second inner scrapers. Furthermore, while the scraper position sensor 108 is configured to monitor the distance between the first and second inner scrapers in the illustrated embodiment, in other embodiments, the scraper position sensor may be configured to monitor the distance between the first and second outer scrapers, thereby enabling the controller to determine an amount of wear on the first outer scraper and/or the second outer scraper based on the distance between the first and second outer scrapers. For example, the scraper position sensor may include a contact sensor coupled to the first and second outer scrapers, and/or the scraper position sensor may include a non-contact sensor (e.g., coupled to another suitable structure of the row unit). Furthermore, in certain embodiments, the sensor assembly may include a first scraper position sensor configured to monitor the distance between the first and second inner scrapers and a second scraper position sensor configured to monitor the distance between the first and second outer scrapers.

Furthermore, in certain embodiments, the sensor assembly may include a scraper position sensor configured to monitor a position of a single scraper (e.g., the position of the distal end of the single scraper) relative to the surface of the respective disc. In such embodiments, the scraper position sensor may be configured to output a sensor signal indicative of the position of the single scraper relative to the surface of the respective disc, and the controller may be configured to determine the amount of wear on the single scraper based on the position of the single scraper relative to the surface of the respective disc. For example, the scraper position sensor may include a contact sensor coupled to a scraper (e.g., and to another suitable structure, such as the frame of the row unit), and the scraper position sensor may be configured to output the sensor signal indicative of the position of the scraper relative to the surface of the respective disc. Additionally or alternatively, the scraper position sensor may include a non-contact sensor (e.g., coupled to the frame of the row unit, coupled to the scraper, etc.), in which the non-contact sensor is configured to output the sensor signal indicative of the position of the scraper relative to the surface of the respective disc. Scraper position sensor(s) may be configured to monitor the position of the first inner scraper 66 relative to the inner surface 68 of the first opener disc 64, the position of the second inner scraper 78 relative to the inner surface 80 of the second opener disc 76, the position of the first outer scraper 58 relative to the outer surface 62 of the first opener disc 64, the position of the second outer scraper 72 relative to the outer surface 74 of the second opener disc 76, the position of another scraper relative to the surface of another disc, or a combination thereof.

The scraper position sensor 108 (e.g., each scraper position sensor) may include any suitable sensor or combination of sensors configured to monitor the position(s) of one or more scrapers. In certain embodiments, the scraper position sensor 108 may include a contact sensor, such as a linear variable differential transformer (LVDT), a linear potentiometer, contact switch(es), another suitable contact sensor, or a combination thereof. For example, in embodiments in which the scraper position sensor is configured to monitor a distance between scrapers, the contact sensor may be coupled to the two scrapers. Furthermore, in embodiments in which the scraper position sensor is configured to monitor the position of a single scraper relative to the surface of the respective disc, the contact sensor may be coupled to the scraper and to another suitable structure of the row unit, such as the frame. Additionally or alternatively, the scraper position sensor 108 may include a non-contact sensor, such as a capacitive sensor, an indicative sensor, an infrared sensor, an optical sensor, an ultrasonic sensor, another suitable non-contact sensor, or a combination thereof. For example, in embodiments in which the scraper position sensor is configured to monitor a distance between scrapers, the non-contact sensor may be positioned between the scrapers (e.g., coupled to a suitable structure of the row unit, such as the frame) and directed toward both scrapers (e.g., a first portion of the non-contact sensor may be directed toward one scraper, and a second portion of the non-contact sensor may be directed toward the other scraper). Furthermore, in embodiments in which the scraper position sensor is configured to monitor a distance between the scrapers, the non-contact sensor may be coupled to one scraper and directed toward the other scraper. In addition, in embodiments in which the scraper position sensor is configured to monitor the position of a single scraper relative to the surface of the respective disc, the non-contact sensor may be coupled to a suitable structure of the row unit, such as the frame, and directed toward the single scraper.

In certain embodiments, the controller is configured to compare the amount of wear on the scraper(s) to a threshold amount of wear, and the controller is configured to output the wear signal only in response to determining that the amount of wear on the scraper(s) is greater than the threshold amount of wear. The threshold amount of wear may be 1 mm, 2 mm, 5 mm, 10 mm, 15 mm, 20 mm, 25 mm, 30 mm, or any other suitable amount of wear. Furthermore, in certain embodiments, the threshold amount of wear may be a percentage of an extent of a contact portion of a scraper (e.g., portion of the scraper configured to contact the surface of the respective disc). For example, the threshold amount of wear may be 1 percent, 2 percent, 5 percent, 10 percent, 15 percent, 20 percent, 30 percent, 40 percent, 50 percent, 60 percent, 70 percent, 80 percent, 90 percent, or any other suitable percentage of the extent of the contact portion of the scraper. While outputting the wear signal only in response to determining that the amount of wear on the scraper(s) is greater than the threshold amount of wear is disclosed above, in certain embodiments, the controller may be configured to output the wear signal without comparing the amount of wear to the threshold amount of wear.

In the illustrated embodiment, the actuator assembly 94 includes two actuators configured to control a magnitude of force applied by each inner scraper to the inner surface of the respective opener disc. Each actuator may be communicatively coupled to the controller, as disclosed above with reference to FIG. 3. The controller is configured to control a first actuator 110 of the actuator assembly 94 to control the magnitude of the force applied by the first inner scraper 66 to the inner surface 68 of the first opener disc 64, and the controller is configured to control a second actuator 111 of the actuator assembly 94 to control the magnitude of the force applied by the second inner scraper 78 to the inner surface 80 of the second opener disc 76. The controller is configured to control each actuator based on the amount of wear on the respective scraper. For example, as each scraper wears, the magnitude of the force applied by the respective biasing member may decrease (e.g., due to elongation of the biasing member). Accordingly, the controller may instruct the respective actuator to compress the biasing member as the scraper wears to substantially maintain the contact force between the respective scraper and the surface of the respective disc.

In the illustrated embodiment, the first actuator 110 is configured to control the force applied by the first biasing member 102 by controlling the compression of the first biasing member 102. For example, the first actuator 110 may control a position of a nut along the first fastener 70 to control the compression of the first biasing member 102. In addition, the second actuator 111 is configured to control the force applied by the second biasing member 104 by controlling the compression of the second biasing member 104. For example, the second actuator 111 may control a position of a nut along the second fastener 106 to control the compression of the second biasing member 104. While each actuator is configured to control the force applied by a respective biasing member in the illustrated embodiment, in other embodiments, at least one actuator may be configured to directly apply the force to the scraper. For example, at least one actuator may include a hydraulic or pneumatic cylinder configured to directly control the force applied by the respective scraper(s) to the respective opener disc(s).

In addition, while the actuator assembly includes two actuator in the illustrated embodiment, in other embodiments, the actuator assembly may include more or fewer actuators (e.g., one actuator for each scraper). For example, in certain embodiments, the actuator assembly may include actuator(s) configured to control magnitude(s) of force applied by the outer scraper(s) to the outer surface(s) of the respective opener disc(s). For example, the controller may be configured to control an actuator that is configured to control a magnitude of force applied by the first outer scraper to the outer surface of the first opener disc, and/or the controller may be configured to control an actuator that is configured to control a magnitude of force applied by the second outer scraper to the outer surface of the second opener disc. Furthermore, the controller may be configured to control the force based on the amount of wear on the respective scraper. For example, as each scraper wears, the magnitude of the force applied by a respective biasing member (e.g., a biasing member of the biasing system) may decrease (e.g., due to elongation of the biasing member). Accordingly, the controller may instruct the respective actuator to compress the biasing member as the scraper wears to substantially maintain the contact force between the respective scraper and the surface of the respective disc. Furthermore, in certain embodiments, the controller may be configured to control an actuator that directly applies force to the respective scraper based on the amount of wear on the respective scraper. In addition, in certain embodiments, at least one of the actuators disclosed above may be omitted (e.g., the actuator assembly may be omitted). In such embodiments, the force applied by the respective scraper to the respective disc may be controlled manually (e.g., by moving the nut along the respective fastener to control compression of the first/second biasing member to control the force applied by the respective inner scraper).

While the scrapers are configured to engage the surfaces of opener discs in the illustrated embodiment, in other embodiments, at least one scraper may be configured to engage the surface of another suitable disc (e.g., coulter disc, closing disc, residue management disc, etc.) to remove accumulated soil from the surface of the disc. Furthermore, while the controller is configured to determine an amount of wear on the scraper based on the position of the scraper relative to the surface of the respective disc in the illustrated embodiment, in other embodiments, the controller may be configured to determine one or more other conditions/properties based on the position of the scraper relative to the surface of the respective disc. For example, in certain embodiments, the controller may be configured to detect substantial soil accumulation on a disc in response to identifying a significant movement of the scraper away from the surface of the respective disc.

In the illustrated embodiment, the sensor assembly 82 includes a first disc speed sensor 112 (e.g., first sensor, first speed sensor) and a second disc speed sensor 114 (e.g., second sensor, second speed sensor). The first disc speed sensor 112 and the second disc speed sensor 114 may be communicatively coupled to the controller, as disclosed above with reference to FIG. 3. Furthermore, the first disc speed sensor 112 is configured to output a first sensor signal (e.g., first speed sensor signal) indicative of a first rotational speed of the first opener disc 64, and the second disc speed sensor 114 is configured to output a second sensor signal (e.g., second speed sensor signal) indicative of a second rotational speed of the second opener disc 76. Each disc speed sensor may include any suitable type of sensor configured to monitor a rotational speed of the respective disc. For example, at least one disc speed sensor may include a wheel in contact with the respective disc and configured to monitor the rotational speed of the respective disc by monitoring the revolution of the wheel. Furthermore, in certain embodiments, at least one disc speed sensor (e.g., optical sensor, magnetic sensor, contact switch, etc.) may be configured to monitor the rotational speed of the respective disc by monitoring a marker of the respective disc. For example, the respective disc may include a suitable marker (e.g., a hole in the disc, a magnet coupled to the disc, a protrusion extending from the disc, etc.), and the disc speed sensor may be configured to output the respective sensor signal in response to detection of the marker. The controller may be configured to determine the rotational speed of the respective disc based on the frequency of detection of the marker.

The controller is configured to determine a rotational speed difference between the first rotational speed of the first opener disc 64 and the second rotational speed of the second opener disc 76. In addition, the controller is configured to detect an operational inefficiency in response to determining that the rotational speed difference is greater than a rotational speed difference threshold value. For example, the rotational speed difference threshold value may be 5 rotations per minute (RPM), 10 RPM, 15 RPM, 20 RPM, or any other suitable rotational speed. Furthermore, in certain embodiments, the rotational speed difference threshold value may be a percentage (e.g., 1 percent, 2 percent, 5 percent, 10 percent, 15 percent, etc.) of the first rotational speed, the second rotational speed, or an average of the first and second rotational speeds.

As previously discussed, the operational inefficiency may include a scraper applying an undesirably large contact force to the surface of the respective disc. For example, if the first inner scraper and/or the first outer scraper applies an undesirably large contact force to the first opener disc, the first rotational speed of the first opener disc may be reduced, as compared to the second rotational speed of the second opener disc. If the rotational speed difference is greater than the rotational speed difference threshold value, the controller may detect an operational inefficiency. Additionally or alternatively, the operational inefficiency may include a worn bearing that facilitates rotation of a respective disc. For example, if the bearing that facilitates rotation of the first opener disc wears, the first rotational speed of the first opener disc may be reduced, as compared to the second rotational speed of the second opener disc. If the rotational speed difference is greater than the rotational speed difference threshold value, the controller may detect an operational inefficiency. Additionally or alternatively, the operational inefficiency may include substantial accumulation of soil between a scraper and the surface of a respective disc. For example, if a substantial amount of soil accumulates between the first inner scraper and the first opener disc and/or between the first outer scraper and the first opener disc, the first rotational speed of the first opener disc may be reduced, as compared to the second rotational speed of the second opener disc. If the rotational speed difference is greater than the rotational speed difference threshold value, the controller may detect an operational inefficiency.

Once the controller detects the operational inefficiency, the controller may output an operational inefficiency signal. In certain embodiments, the operational inefficiency signal may be output to the user interface, and the user interface may inform the operator of the implement of the detected operational inefficiency (e.g., by presenting an indication on the display), thereby enabling the operator to perform maintenance operations (e.g., adjusting the force applied by a biasing member to a scraper engaged with a respective disc, manually removing accumulated soil from one of the discs, replacing a worn bearing that facilitates rotation of a respective disc, etc.). As a result, the opener discs may rotate at substantially the same speed (e.g., in which the rotational speed difference is less than or equal to the rotational speed difference threshold value), thereby enhancing formation of the trench within the soil.

In certain embodiments, the controller is configured to control the first actuator 110 of the actuator assembly 94 to control the magnitude of the force applied by the first inner scraper 66 to the inner surface 68 of the first opener disc 64, and/or the controller is configured to control the second actuator 111 of the actuator assembly 94 to control the magnitude of the force applied by the second inner scraper 78 to the inner surface 80 of the second opener disc 76. Furthermore, in certain embodiments, the controller is configured to control an actuator that is configured to control a magnitude of force applied by the first outer scraper to the outer surface of the first opener disc, and/or the controller is configured to control an actuator that is configured to control a magnitude of force applied by the second outer scraper to the outer surface of the second opener disc. The controller may be configured to control the force applied by each scraper based on the rotational speed difference. For example, if the rotational speed difference is greater than the rotational speed difference threshold value, the controller may determine which opener disc is rotating at the slower speed. The controller may then instruct the actuator(s), which are configured to control the magnitude of the force applied by the respective scraper(s) to the slower opener disc, to reduce the magnitude of the applied force. As a result, the rotational speed of the slower opener disc may increase. Furthermore, in certain embodiments, the controller may be configured to control actuator(s) that directly apply force to the respective scraper(s) based on the rotational speed difference. In addition, in certain embodiments, at least one of the actuators disclosed above may be omitted (e.g., the actuator assembly may be omitted). In such embodiments, the force applied by the respective scraper to the respective disc may be controlled manually (e.g., by moving the nut along the respective fastener to control compression of the first/second biasing member to control the force applied by the respective inner scraper).

In the illustrated embodiment, the first disc speed sensor 112 is coupled to the first outer scraper 58, and the second disc speed sensor 114 is coupled to the second outer scraper 72. However, in other embodiments, the first disc speed sensor and/or the second disc speed sensor may be coupled to any other suitable portion of the row unit. For example, in certain embodiments, the first disc speed sensor may be coupled to the first inner scraper, and/or the second disc speed sensor may be coupled to the second inner scraper. Furthermore, in certain embodiments, at least one of the first disc speed sensor or the second disc speed sensor may be coupled to the frame of the row unit. While the disc speed sensors are configured to monitor the rotational speeds of opener discs in the illustrated embodiment, in other embodiments, the disc speed sensors may be configured to monitor the rotational speeds of other suitable discs (e.g., alone or in combination with the opener discs), such as a pair of coulter discs positioned proximate to one another, a pair of soil conditioning discs positioned proximate to one another, a pair of closing discs positioned proximate to one another, another suitable pair of discs, or a combination thereof. Furthermore, in certain embodiments, the sensor assembly may include additional disc speed sensor(s) configured to monitor the rotational speed of additional respective disc(s), and the controller may be configured to determine the rotational speed deference between any of the monitored discs.

In the illustrated embodiment, the sensor assembly 82 includes a soil sensor 116 positioned proximate to the first opener disc 64 and remote from the soil. As used herein, "remote from the soil" refers to positioning the soil sensor such that the soil sensor does not engage the soil during operation of the implement. In the illustrated embodiment, the soil sensor 116 is configured to receive soil from the inner surface 68 of the first opener disc 64 as the first opener disc 64 rotates. In addition, the soil sensor 116 is configured to output a sensor signal indicative of at least one property of the soil (e.g., moisture content of the soil, nutrient content of the soil, firmness of the soil, etc.). Because the soil sensor 116 is positioned remote from the soil, the longevity of the soil sensor may be significantly increased, as compared to a soil sensor that engages the soil during operation of the implement.

As previously discussed, the soil sensor 116 may be communicatively coupled to the controller, as disclosed above with reference to FIG. 3. The controller is configured to receive the sensor signal from the soil sensor 116 and to determine the at least one property of the soil based on the sensor signal. The controller is also configured to output a soil property signal indicative of the at least one soil property. In certain embodiments, the soil property signal may be output to the user interface, and the user interface may inform the operator of the at least one soil property (e.g., the display of the user interface may present a visual indication of the at least one soil property), thereby enabling the operator to manually adjust operation of the implement based on the at least one soil property. Furthermore, in certain embodiments, the controller may control one or more actuators based on the at least one soil property. In such embodiments, the soil property signal may be output to one or more actuators, and the soil property signal may be indicative of instructions to control the one or more actuators to adjust operation of the implement. For example, the controller may control one or more downforce actuators based on a detected moisture content of the soil, the controller may control one or more metering actuators to control seed spacing based on a detected nutrient content of the soil, the controller may control one or more penetration depth actuators based on a firmness of the soil, the controller may control other suitable actuator(s) based on certain soil property/properties, or a combination thereof.

The soil sensor may include any suitable type of sensor (e.g., contact sensor or non-contact sensor) configured to monitor one or more properties of the soil. For example, in certain embodiments, the soil sensor may include a soil resistivity sensor configured to monitor conductivity of the soil (e.g., which may be indicative of soil moisture content, soil nutrient content, etc.). Furthermore, in certain embodiments, the soil sensor may include an optical soil sensor (e.g., infrared sensor, camera, etc.) configured to monitor optical properties of the soil (e.g., which may be indicative of soil nutrient content, soil density, etc.). In certain embodiments, the soil sensor may include a spectrometer configured to monitor the chemical composition of the soil.

While the soil sensor 116 is coupled to the first inner scraper 66 and configured to receive soil from the inner surface 68 of the first opener disc 64 in the illustrated embodiment, in other embodiments, the soil sensor may be coupled to any other suitable portion of the row unit and/or configured to receive soil from any other suitable opener disc surface. For example, in certain embodiments, the soil sensor may be coupled to the first outer scraper 58 and configured to receive soil from the outer surface 62 of the first opener disc 64, the soil sensor may be coupled to the second inner scraper 78 and configured to receive soil from the inner surface 80 of the second opener disc 76, or the soil sensor may be coupled to the second outer scraper 72 and configured to receive soil from the outer surface 74 of the second opener disc 76. Furthermore, in certain embodiments, the soil sensor may be coupled to another suitable element of the row unit (e.g., the frame of the row unit) and configured to receive soil from any suitable surface of any suitable opener disc. In addition, while the sensor assembly includes a single soil sensor in the illustrated embodiment, in other embodiments, the sensor assembly may include more or fewer soil sensors (e.g., 0, 1, 2, 3, 4, or more), in which each soil sensor is positioned at a suitable location on the row unit to receive soil from a respective surface of a respective disc. Furthermore, while the soil sensor is configured to receive soil from the surface of an opener disc in the illustrated embodiment, in other embodiments, the soil sensor may be configured (e.g., positioned) to receive soil from the surface of another suitable disc, such as a coulter disc, a closing disc, a packer wheel, or a residue manager disc, among other suitable discs.

While the sensor assembly includes one or more scraper position sensors, disc speed sensors, and one or more soil sensors in the illustrated embodiment, in other embodiments, at least one type of sensor may be omitted. For example, in certain embodiments, the sensor assembly may include one or two of the scraper position sensor(s), the disc speed sensors, or the soil sensor(s). Furthermore, while the scraper assembly 56 includes an inner scraper and an outer scraper for each opener disc in the illustrated embodiment, in other embodiments, at least one inner scraper and/or at least one outer scraper may be omitted. Furthermore, in certain embodiments (e.g., embodiments including the disc speed sensors and/or the soil sensor), all of the scrapers may be omitted. While the monitoring system is disclosed above with regard to a row unit of a planting implement, the monitoring system disclosed herein may be utilized with any other suitable type of row unit (e.g., seeding row unit, etc.). In addition, the monitoring system disclosed herein may be utilized to monitor scraper wear, an operational inefficiency associated with a disc rotational speed differential, at least one soil property, or a combination thereof, on another suitable portion of an implement (e.g., separate from a row unit, on an implement that does not include row units, etc.). For example, a soil sensor may be positioned proximate to a disc of a tillage implement and remote from the soil to monitor at least one soil property. By way of further example, a scraper position sensor may be configured to monitor a position of at least one scraper relative to a surface of at least one respective tillage disc.

While only certain features have been illustrated and described herein, many modifications and changes will occur to those skilled in the art. It is, therefore, to be understood that the appended claims are intended to cover all such modifications and changes as fall within the true spirit of the disclosure.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

The invention claimed is:

1. A monitoring system for an agricultural implement, comprising:
a sensor configured to output a sensor signal indicative of a position of at least one scraper of the agricultural implement relative to a surface of at least one respective disc corresponding to an amount of wear on the at least one scraper due to contact between the at least one scraper and the surface of the at least one respective disc, wherein the at least one scraper is configured to engage the surface of the at least one respective disc to remove accumulated soil from the surface of the at least one respective disc; and
a controller comprising a memory and a processor, wherein the controller is communicatively coupled to the sensor, the controller is configured to determine the amount of wear on the at least one scraper based on the position of the at least one scraper relative to the surface of the at least one respective disc, and the controller is configured to output a wear signal indicative of the amount of wear on the at least one scraper.

2. The monitoring system of claim 1, wherein the sensor is configured to couple to the at least one scraper.

3. The monitoring system of claim 2, wherein the sensor comprises a linear variable differential transformer (LVDT).

4. The monitoring system of claim 1, wherein the at least one scraper comprises a first inner scraper and a second inner scraper, the at least one respective disc comprises a first respective disc and a second respective disc, the first inner scraper is configured to engage the surface of the first respective disc, the second inner scraper is configured to engage the surface of the second respective disc, the sensor signal indicative of the position of the at least one scraper relative to the surface of the at least one respective disc is indicative of a distance between the first inner scraper and the second inner scraper, and the controller is configured to determine the amount of wear on the first inner scraper, the second inner scraper, or a combination thereof, based on the distance between the first inner scraper and the second inner scraper.

5. The monitoring system of claim 4, wherein the sensor is configured to couple to the first inner scraper and to the second inner scraper.

6. The monitoring system of claim 1, wherein the controller is configured to compare the amount of wear on the at least one scraper to a threshold amount of wear, and the controller is configured to output the wear signal only in response to determining that the amount of wear on the at least one scraper is greater than the threshold amount of wear.

7. The monitoring system of claim 1, comprising an actuator configured to control a magnitude of force applied by the at least one scraper to the surface of the at least one respective disc, wherein the actuator is communicatively coupled to the controller, and the wear signal indicative of the amount of wear on the at least one scraper is indicative of instructions to control the magnitude of the force applied by the at least one scraper to the surface of the at least one respective disc.

8. A monitoring system for an agricultural implement, comprising:
   a sensor configured to output a sensor signal indicative of a distance between a first inner scraper and a second inner scraper of the agricultural implement, wherein the first inner scraper is configured to engage a surface of a first respective disc to remove accumulated soil from the surface of the first respective disc, and the second inner scraper is configured to engage a surface of a second respective disc to remove accumulated soil from the surface of the second respective disc; and
   a controller comprising a memory and a processor, wherein the controller is communicatively coupled to the sensor, the controller is configured to determine an amount of wear on the first inner scraper, the second inner scraper, or a combination thereof, based on the distance between the first inner scraper and the second inner scraper, and the controller is configured to output a wear signal indicative of the amount of wear.

9. The monitoring system of claim 8, wherein the sensor is configured to couple to the first inner scraper and to the second inner scraper.

10. The monitoring system of claim 9, wherein the sensor comprises a linear variable differential transformer (LVDT).

11. The monitoring system of claim 8, wherein the controller is configured to compare the amount of wear to a threshold amount of wear, and the controller is configured to output the wear signal only in response to determining that the amount of wear is greater than the threshold amount of wear.

12. The monitoring system of claim 8, comprising:
   a first actuator configured to control a magnitude of force applied by the first inner scraper to the surface of the first respective disc, wherein the first actuator is communicatively coupled to the controller; and
   a second actuator configured to control a magnitude of force applied by the second inner scraper to the surface of the second respective disc, wherein the second actuator is communicatively coupled to the controller;
   wherein the wear signal is indicative of instructions to control the magnitude of the force applied by the first inner scraper to the surface of the first respective disc, to control the magnitude of the force applied by the second inner scraper to the surface of the second respective disc, or a combination thereof.

* * * * *